United States Patent [19]

Tsien et al.

[11] Patent Number: 5,602,258

[45] Date of Patent: Feb. 11, 1997

[54] AZIDE-CONTAINING CHELATORS WHOSE AFFINITY FOR CALCIUM ION IS DECREASED BY ILLUMINATION

[75] Inventors: Roger Y. Tsien, La Jolla; Stephen R. Adams, Poway, both of Calif.

[73] Assignee: The Regents of University of California, Oakland, Calif.

[21] Appl. No.: 968,002

[22] Filed: Oct. 23, 1992

[51] Int. Cl.⁶ ............................................... C07D 263/30
[52] U.S. Cl. ............................ 548/235; 548/236; 552/1
[58] Field of Search ........................... 548/235, 236; 552/1

[56] References Cited

U.S. PATENT DOCUMENTS

| | | | |
|---|---|---|---|
| 4,603,209 | 7/1986 | Tsien et al. | 548/236 |
| 4,689,432 | 8/1987 | Tsien et al. | 562/435 |
| 4,806,604 | 2/1989 | Tsien et al. | 549/439 |
| 5,134,232 | 7/1992 | Tsien et al. | 540/467 |
| 5,141,627 | 8/1992 | Tsien et al. | 204/157.88 |

OTHER PUBLICATIONS

Joseph P. Y. Kao et al., "Photochemically Generated Cytoslic Calcium Pulses and Their Detection by Fluo–3*", *The Journal of Biological Chemistry*, May 1989, vol. 264, No. 14, pp. 8179–8184.

Jack H. Kaplan, "Photochemical Manipulation of Divalent Cation Levels", *Annu. Rev. Physiol.*, 1990, vol. 52, pp. 897–914.

Alison M. Gurney et al, "Light–Flash Physiology with Synthetic Photosensitive Compounds", *Physiological Reviews*, Apr. 1987, vol. 67, No. 2, pp. 583–617.

Roger Y. Tsien, "New Calcium Indicators and Buffers with High Selectivity Against Magnesium and Protons: Design, Synthesis, and Properties of Prototype Structures", *Journal of the American Chemical Society*, 1980, vol. 19, No. 11, pp. 2396–2404.

Akawasi Minta et al., "Fluorescent Indicators for Cytosolic Calcium Based on Rhodamine and Fluorescein Chromophores*", *The Journal of Biological Chemistry*, May 15, 1989, vol. 264, No. 14, pp. 8171–8178.

Roger Y. Tsien et al., "Control of Cytoplasmic Calcium with Photolabile Tetracarboxylate 2–Nitroobenzhydrol Chelators", *Biophysical Journal*, Nov. 1986, vol. 50, pp. 843–853.

G. C. R. Ellis–Davies et al., "A New Class of Photolabile Chelators for the Rapid Release of Divalent Cations: Generation of Caged Ca and Caged Mg", *Journal of Organic Chemistry*, 1988, vol. 53, No. 9, pp. 1966–1969.

S. R. Adams et al., "Biologically Useful Chelators That Release $Ca^{2+}$ Upon Illumination", *Journal of the American Chemical Society*, 1988, vol. 110, No. 10, pp. 3212–3220.

James A. McCray et al., "Properties and Uses of Photoreactive Caged Compounds", *Annu. Rev. Biophys. Chem.*, 1989, vol. 18, pp. 239–270.

Grzegorz Grynkiewicz et al., "A New Generation of $Ca^{2+}$ Indicators with Greatly Improved Fluorescence Properties", *The Journal of Biological Chemistry*, Mar. 25, 1985, vol. 260, No. 6, pp. 3440–3450.

*Primary Examiner*—Sharon A. Gibson
*Assistant Examiner*—Catherine Scalzo
*Attorney, Agent, or Firm*—Phillips, Moore, Lempio & Finley

[57] ABSTRACT

The present invention relates to a group of organic chelators whose affinity for calcium ion in solution is decreased by electromagnetic radiation. Specifically, the chelators are related to fura-2 and utilize the addition of an azide group to the 3-position of the benzofuron ring of a fura-2 type structure. Photolysis of the azide group causes the calcium ion affinity to decrease 100 to 1000 fold. These chelators when incorporated into rat fibroblasts either by microinjection or by incubation as the membrane-permeable, enzymatically-labile esters and flash-photolyzed cause large increases in intracellular free calcium ion. These chelators are used to generate controlled fast elevation of intracellular free calcium ion concentration to mimic or modulate a number of important cellular responses, especially in nerve or muscle.

21 Claims, 5 Drawing Sheets

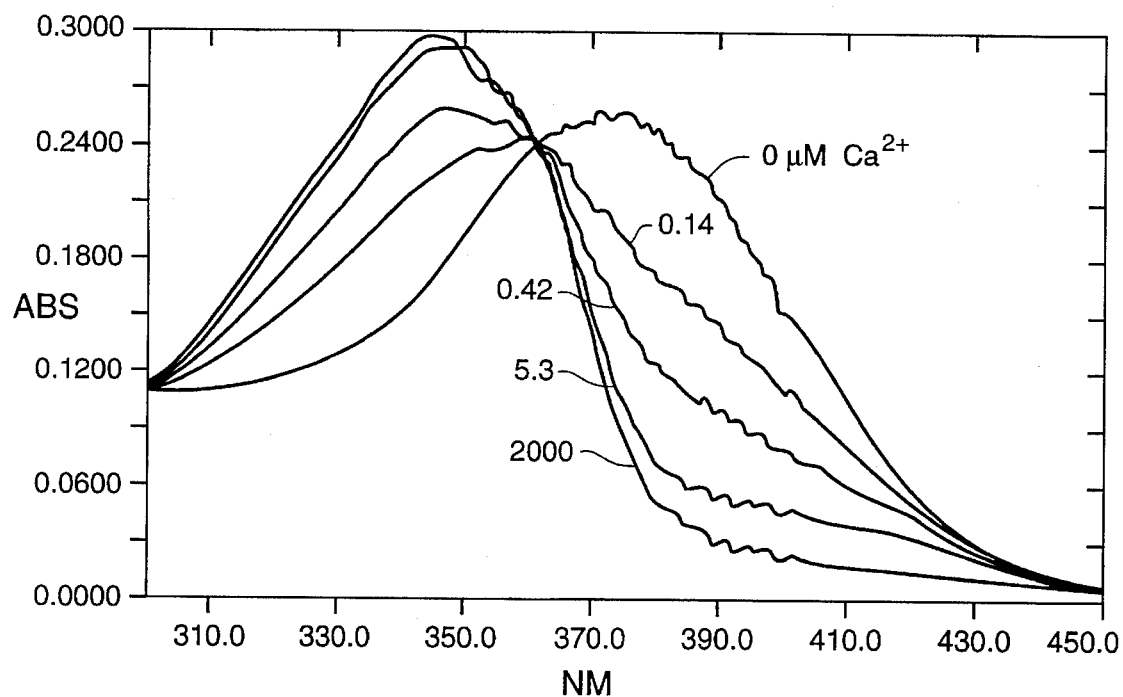
FIG._1A
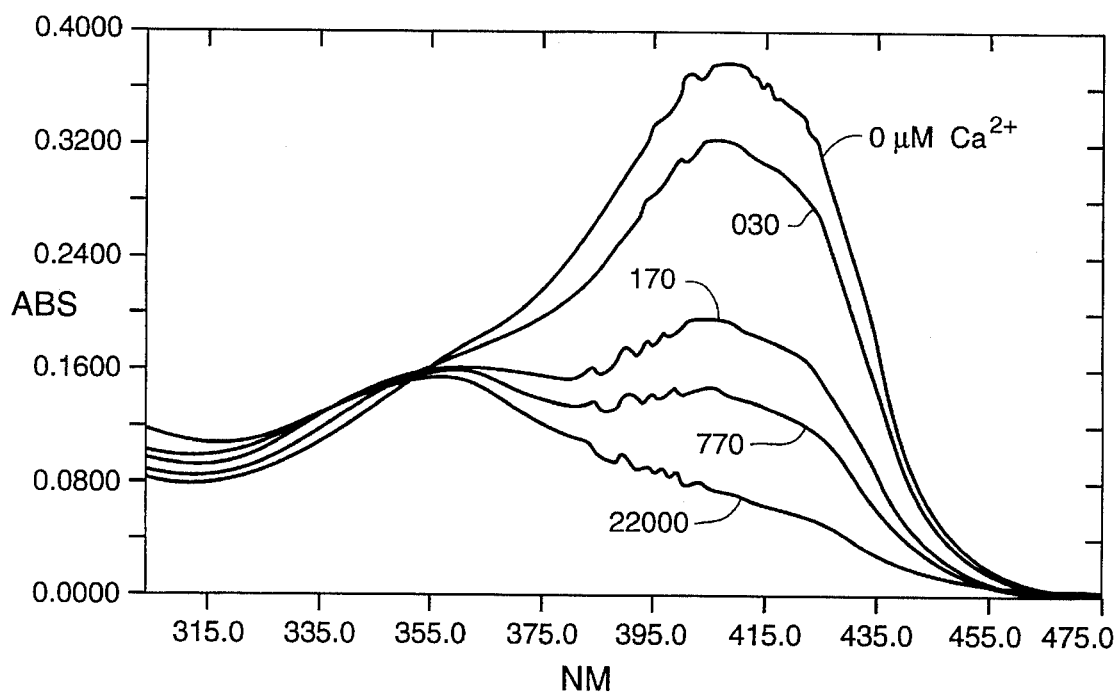
FIG._1B

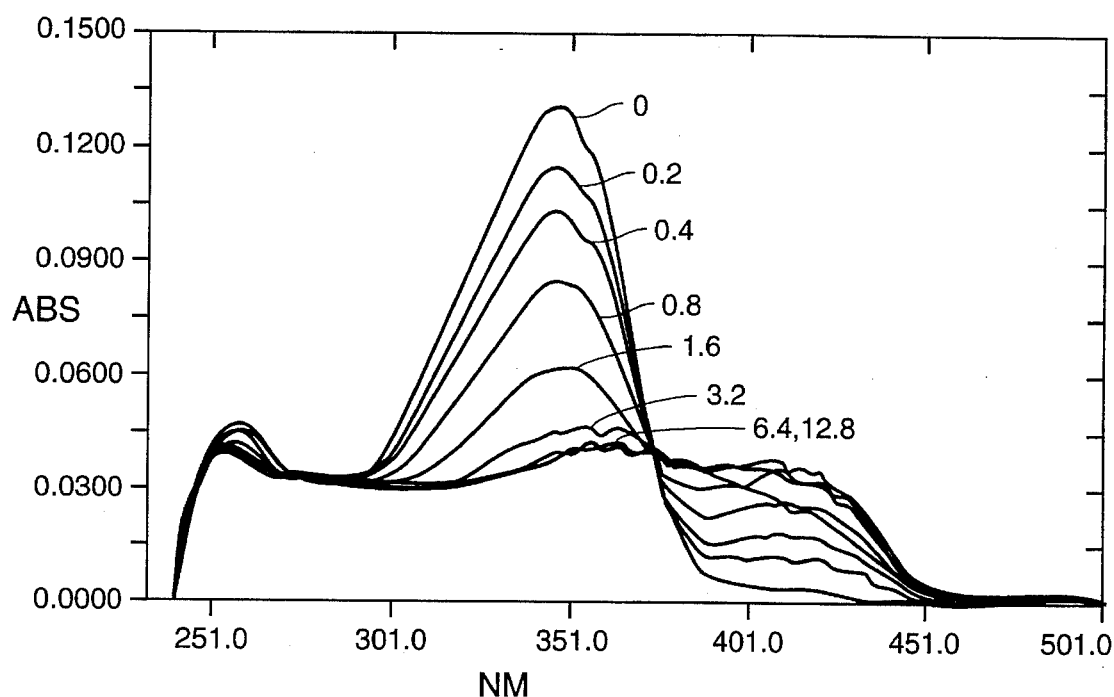
FIG._2A
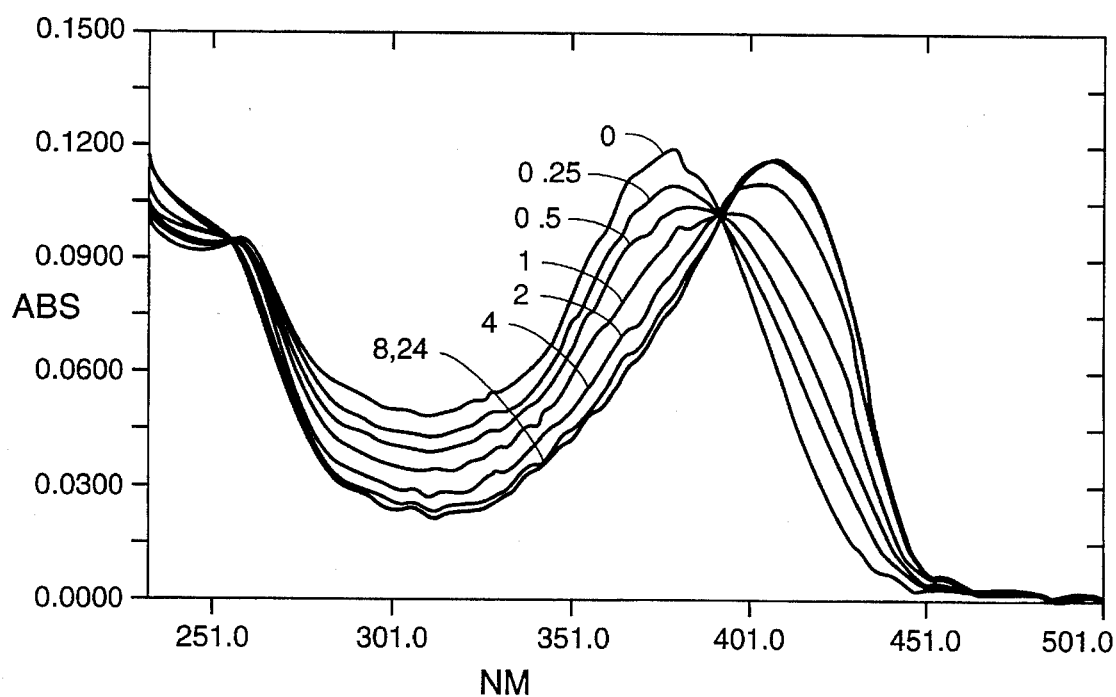
FIG._2B

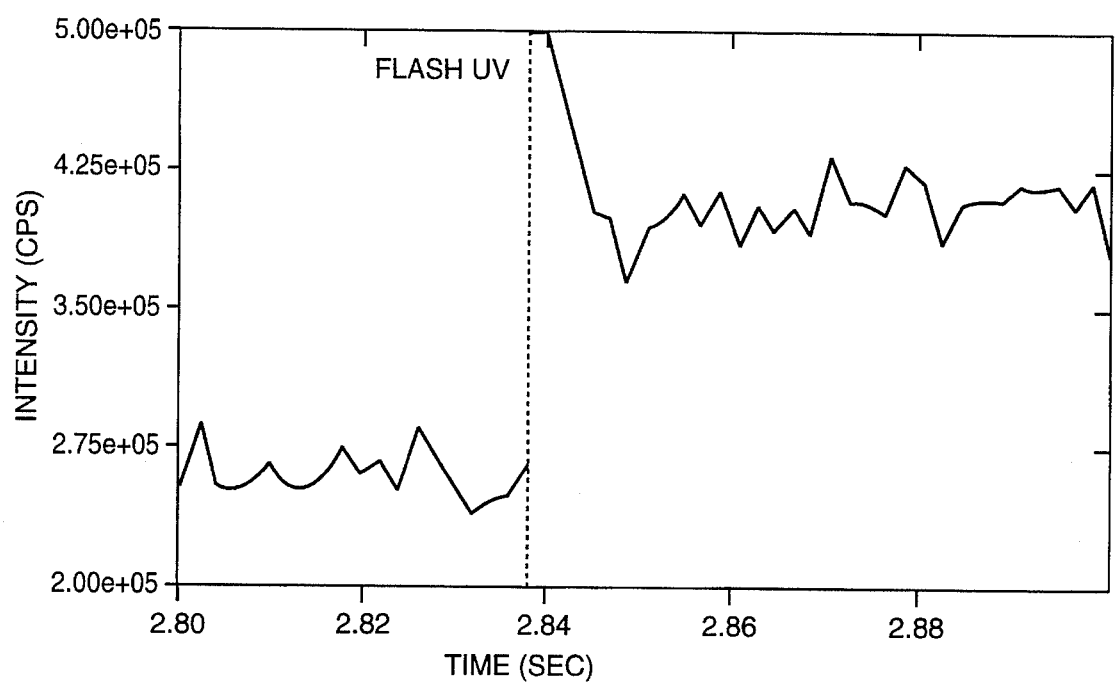
FIG._3
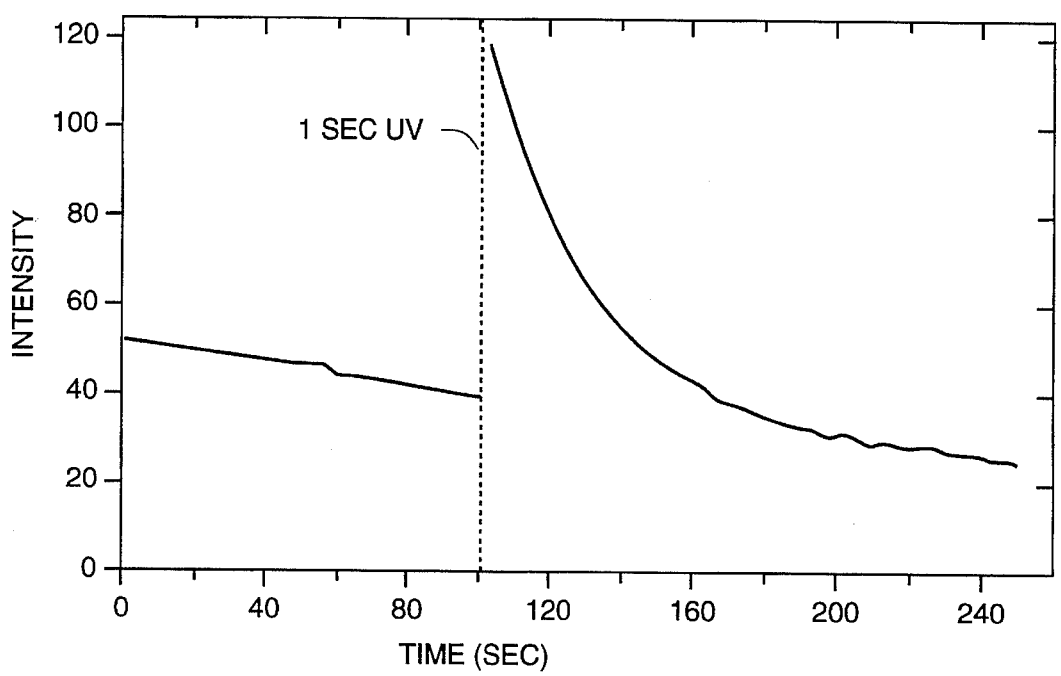
FIG._4

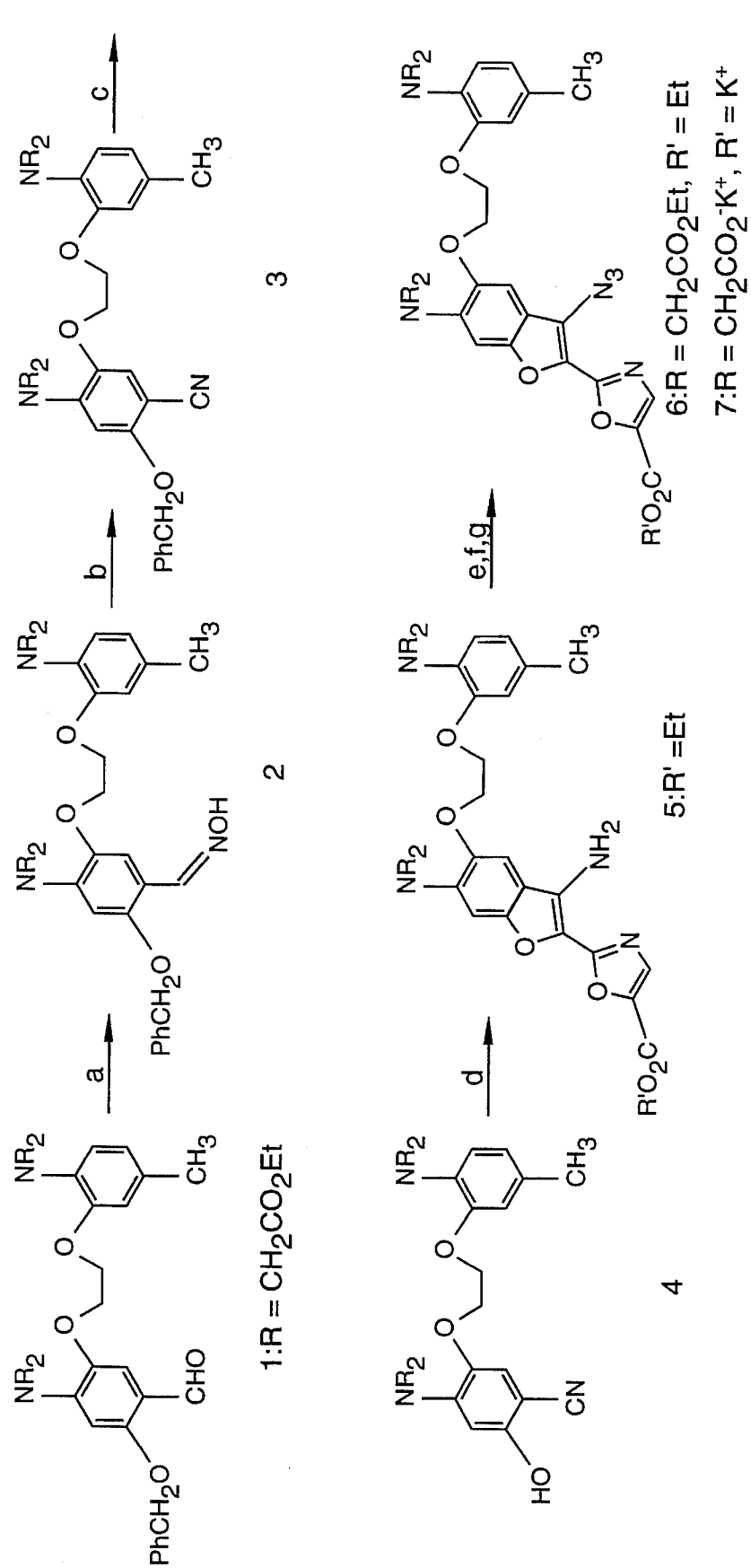
FIG._5

| Photolabile Chelator | $K_D$ for $Ca^{2+}$ (μM) before | $K_D$ for $Ca^{2+}$ (μM) after hv | $K_D$ for $Mg^{2+}$ (mM) before hv | Quantum Yield Q | Extinction Coefficient $\epsilon$ ($M^{-1}cm^{-1}$) | $Q\epsilon$ ($M^{-1}cm^{-1}$) |
|---|---|---|---|---|---|---|
| nitr-5 | 0.145 | 6.3 | 8.5 | 0.035 | 5,500 | 190 |
| DM-nitrophen | 0.005 | 3,000 | 0.005 | 0.18 | 4,330 | 780 |
| nitr-8 | 0.45 | 1,370 | | 0.026 | 11,000 | 286 |
| azid-1 | 0.21 | 110 | 7.6 | 1.0 | 33,000 | 33,000 |

AZIDE-CONTAINING CHELATORS WHOSE AFFINITY FOR CALCIUM ION IS DECREASED BY ILLUMINATION

ORIGIN OF THE INVENTION

The present invention resulted from research with U.S. Government grant support under NS27177 awarded by the U.S. Department of Health and Human Resources. The U.S. Government has the certain rights in this invention.

FIELD OF THE INVENTION

The present invention relates to photosensitive calcium ion ($Ca^{+2}$) chelators whose affinity for calcium is decreased by illumination. More specifically, the present invention concerns the illumination of novel compounds, e.g. tetraacetic acid substituted aniline-type structures which bear one or more azide substituents and are connected by an alkylenedioxy or cyclic dioxy linkage. A heteroaromatic group covalently bonded to the carbon atom adjacent to the oxygen of a benzofuran structure is preferred. The preparation of these novel compounds is described herein.

DESCRIPTION OF RELATED ART

The recent introduction of photosensitive derivatives of nucleotides, inositol polyphosphates, neurotransmitters, calcium and protons which release the physiologically active compound with a flash of light, has enabled the dynamics of biological responses to be probed non-invasively within cells on a microsecond or millisecond time scale. The photochemical manipulation of intracellular free $Ca^{2+}$ concentration ($[Ca^{2+}]_i$) first become possible with the introduction of the "nitr" series of chelators which release $Ca^{2+}$ upon illumination with long wavelength UV light. See for example, R. Y. Tsien, et al., U.S. Pat. Nos. 4,589,432 and 4,806,604. Thus, when loaded into cells either through microinjection or through incubation with the membrane-permeant acetoxymethyl ester, the nitr compounds can be irradiated to generate spikes or plateaus of elevated $[Ca^{2+}]_i$. For example, nitr-5 has been used in cultured rat sympathetic neurons to study the activation stoichiometry and kinetics of the $Ca^{2+}$-activated $K^+$-conducting channel, and in skeletal muscle to examine the kinetics of $Ca^{2+}$ regulation to troponin C.

The present invention describes synthesis, characterization and biological application of a series of chelators whose $Ca^{2+}$ affinity is decreased upon photolysis, an effect which is more pronounced than that exhibited by the "nitr" series of photolabile $Ca^{2+}$ chelators. Therefore, these chelators can generate a larger rise in $[Ca^{2+}]$. The new series of chelators like the nitr series, are based on the parent $Ca^{2+}$ chelators, BAPTA and fura-2 and retain their high selectivity for $Ca^{2+}$ over $Mg^{2+}$, their insensitivity to pH variations above pH 7, and their fast $Ca^{2+}$ binding kinetics.

The ideal "caged" $Ca^{2+}$ chelator should fulfill the following requirements:

(1) The initial $Ca^{2+}$ affinity of the chelator before photolysis should be as strong as possible but certainly with dissociation constant $K_d$ less greater than $10^{-6}M$ with at least four orders of magnitude of selectivity for $Ca^{2+}$ and $Mg^{2+}$ (2) After photochemical conversion, the chelator $K_d$ should be as high as possible.

(3) The photochemistry and $Ca^{2+}$ uptake should be complete in $\leq 10^{-3}$ s;

(4) The wavelength and intensity of the light required for photolysis should not significantly perturb the cells; and (5) The photochemistry should not generate toxic byproducts or other biologically active substances.

The present invention achieves the above requirements.

DESCRIPTION OF THE RELATED ART

The following art is of general and specific interest in this application.

S. R. Adams, et al. (1988) *J. Am. Chem. Soc.*, Vol. 110; pp. 3212 to 3220.

G. Grynkiewicz, et al. (1985) *Journal of Biological Chemistry*, Vol. 260, pp. 3440–3450.

G. C. R. Ellis-Davies, et al. (1988) *J. Organic Chem.*, Vol. 53, pp. 1966 to 1969.

A. M. Gurney, et al. (1987) *Physiological Reviews*, Vol. 67, pp. 583–617.

J. H. Kaplan, (1990) *Annual Rev. Physiol.* Vol. 52, pp. 897 to 914.

J. H. Kaplan, et al. (1988) *Proc. Natl. Acad. Sci. USA*, Vol. 85, pp. 6571 to 6575.

J. P. Y. Kao, et al. (1989) *Journal of Biological Chemistry*, Vol. 264, pp. 8179–8184.

J. A. McCray, et al. (1989) *Annual Review of Biophysics and Biophysical Chemistry*, Vol. 18, pp. 239–270.

P. A. Minta, et al. (1989) *Journal of Biological Chemistry*, Vol. 264, pp. 8171–8178.

R. Y. Tsien, (1980) *Biochemistry*, Vol. 264, pp. 8171–8178.

R. Y. Tsien, et al. (1986) *Biophys. Journal*, Vol. 50, pp. 843 to 853.

R. Y. Tsien, et al., U.S. Pat. No. 4,603,209, issued Jul. 29, 1986.

R. Y. Tsien, et al., U.S. Pat. No. 4,689,432, issued Aug. 25, 1987.

R. Y. Tsien, et al., U.S. Pat. No. 4,806,604, issued Feb. 21, 1989.

R. Y. Tsien, et al., U.S. Pat. No. 5,134,232, issued Jul. 28, 1992.

R. Y. Tsien, et al., U.S. Pat. No. 5,141,627, issued Aug. 25, 1992.

All of the references and patents cited herein are expressly incorporated by reference in this application.

It is an object of the present invention to use the adjustment of the $Ca^{2+}$ affinity of BAPTA by suitable substitution of the aromatic and heteroaromatic rings present. New chelators (e.g., the mono- or diazide series) incorporate an azide group which on photolysis produces an electron-withdrawing substituent. Therefore, a chelator with an initially high affinity for $Ca^{2+}$ is photochemically converted to one having low affinity without steric modification of the metal binding site.

SUMMARY OF THE INVENTION

The present invention relates to compounds whose affinity for calcium ion is decreased by exposure to electromagnetic radiation. Specifically, calcium chelators are described which are generally structurally similar to fura-2 having at least one azide group on the 3-position of the benzofuran ring of the fura-2-type structure. These compounds are converted by ultraviolet irradiation to products whose calcium affinities have been decreased by two to five orders of magnitude.

Thus, the present invention relates to a compound of the formula:

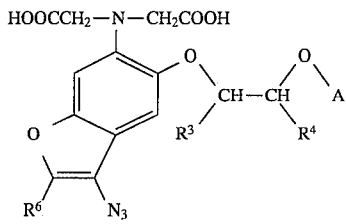 (I)

and the pharmaceutically acceptable non-toxic salts and esters thereof, wherein:

A is independently selected from:

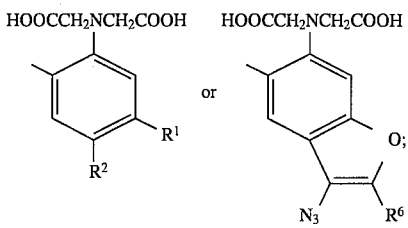

$R^1$ and $R^2$ are each independently selected from the group consisting of —H, C1 to C4 alkyl, —F, —Cl, —Br, C1 to C4 alkoxy, —NO$_2$, —COO$^-$, and —NH(C=O)R$^5$ where $R^5$ is —H, or C1 to C18 alkyl;

$R^3$ and $R^4$ are each independently —H, C1 to C4 alkyl, —CH$_2$OH, —COOH, or $R^3$ and $R^4$ together are —(CH$_2$)$_m$—Y—(CH$_2$)$_n$— where m and n are each independently 1 or 2, and Y is independently selected from —CH$_2$—, —O—, —S—, —S—S—, or —NR$^5$, where $R^5$ is —H, or C1 to C18 alkyl; and $R^6$ is a heteroaromatic group having at least one 5-membered or 6-membered heteroaromatic group or combinations thereof, the heteroaromatic group containing at least one sp$^2$-hydridized nitrogen atom at the ∝-position to the carbon atom attached to the benzofuran, the heteroaromatic group having substitutents at 0, 1 or 2 ring positions. Preferably, the substitutents are independently selected from —COOH or —CH$_2$COOH.

In a preferred embodiment, A is

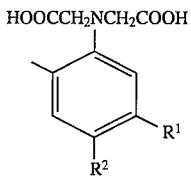

and $R^1$ is hydrogen.

In a more preferred embodiment, $R^6$ is selected from:

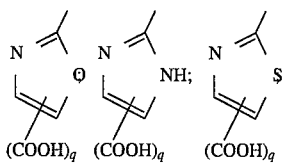

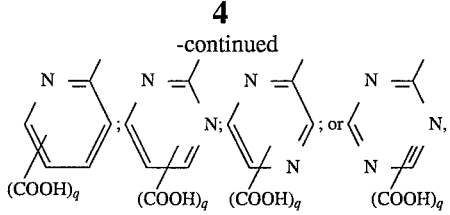

and q is 0, 1 or 2.

$R^6$ is especially preferred as:

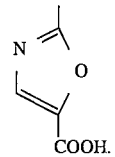

In another embodiment A is:

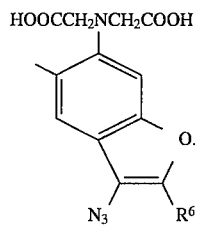

In a preferred embodiment of the benzofuran, $R^6$ is independently selected from:

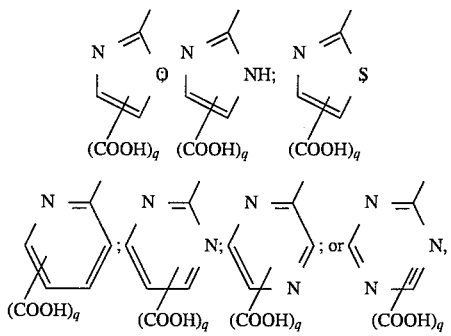

and q is 0, 1 or 2.

$R^6$ is especially preferred as:

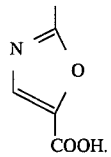

Preferred embodiments also include the free acids, salts, and esters, especially the ethyl, propyl, butyl and acetoxymethyl esters.

In another aspect the present invention relates to a method for the releasing of calcium ion in solution, which method comprises:

(a) contacting a sample containing calcium ion with an effective quantity of the generic compound of structure (I) described above;

(b) irradiating the solution obtained with electromagnetic radiation effective to convert the azide moiety and decrease the activity of the calcium ion chelating agent.

BRIEF DESCRIPTION OF THE FIGURES

FIG. 1A shows the absorbance of unphotolyzed Azid-1 as a function of free [$Ca^{2+}$].

FIG. 1B shows the absorbance of photolyzed Azid-1 as a function of free [Ca].

FIG. 2A shows absorbance spectra of Azid-1 undergoing photolysis in the presence of $Ca^{2+}$.

FIG. 2B shows absorbance spectra of Azid-1 undergoing photolysis in the absence of $Ca^{2+}$.

FIG. 3 is a flash photolysis record showing the kinetics of generating low affinity chelator as signaled by increased fluorescence emission of the $Ca^{2+}$-indicator, fluo-3.

FIG. 4 shows a record of the rapid increase in intracellular free $Ca^{2+}$ produced by flash photolysis of Azid-1 in a Fisher rat embryo fibroblast cell.

FIG. 5 shows one reaction sequence used to produce compounds of the present invention.

FIG. 6 is Table 1 which compares the $Ca^{2+}$-binding and light-sensitivity of chelators whose affinity for $Ca^{2+}$ is decreased by illumination. For more details see S. R. Adams, et al., 1988; J. R. Kaplan, 1990. The data on nitr-8 are unpublished observations of S. R. Adams and R. Y. Tsien.

DETAILED DESCRIPTION OF THE INVENTION AND PREFERRED EMBODIMENTS

As used herein:

"BAPTA" refers to 1,2-bis (ortho-aminophenoxy) ethane-N, N,N',N'-tetraacetic acid;

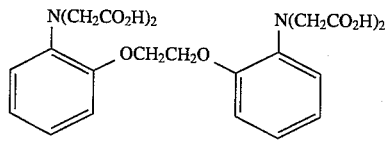

"[$Ca^{2+}$]$_i$" refers to cytosolic free $Ca^{2+}$ concentration;
"Fura-2" refers to the following structure:

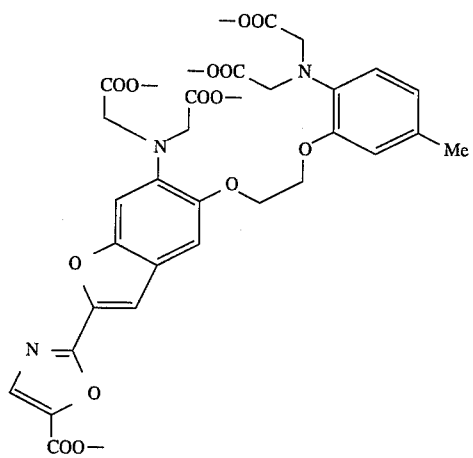

"PHARMACOLOGICALLY ACCEPTABLE SALT AND/OR ESTER" refers to a chemical derivative of compound of structure (I) which is recognized in the art as being useful to determine the pharmacology of a compound. It may or may not be pharmaceutically acceptable and/or non-toxic.

"PHARMACEUTICALLY ACCEPTABLE SALT" refers to those salts which retain the biological effectiveness and properties of the free acids and which are not biologically or otherwise undesirable, formed with inorganic bases such as sodium hydroxide, potassium hydroxide, ammonium hydroxide and the like.

"PHARMACEUTICALLY ACCEPTABLE ESTER" of the compound of formula I which may conveniently be used in therapy includes those containing the alkanoyloxy group, —O—C(=O) —Z, wherein Z is an alkyl, acyloxyalkyl, or aminoalkyl group containing 1 to 18 carbon atoms, i.e., the carboxyl group has been esterified. The group, Z, may be for example, methyl, ethyl, butyl, hexyl, octyl, dodecyl, acetoxymethyl 1-acetoxyethyl, formyloxymethyl, pivaloyloxymethyl, dimethylaminoethyl, diethylaminoethyl and the like. This invention contemplates those compounds of formula I which are esters as described herein and at the same time are the pharmaceutically acceptable acid addition salts thereof.

This invention is a significant improvement over the existing state of the art described in the references listed herein above. It utilizes photoreactive azide groups to generate the change in calcium affinity of the chelator upon irradiation. In contrast, the conventional nitrobenzyl photochemistry is used in all the prior art, namely, "nitr" chelators and DM-nitrophen.

The Azid-1 structure shown below:

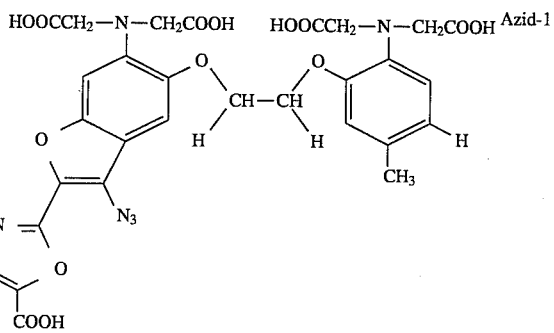

and the Azid-2 Dimer structure shown below:

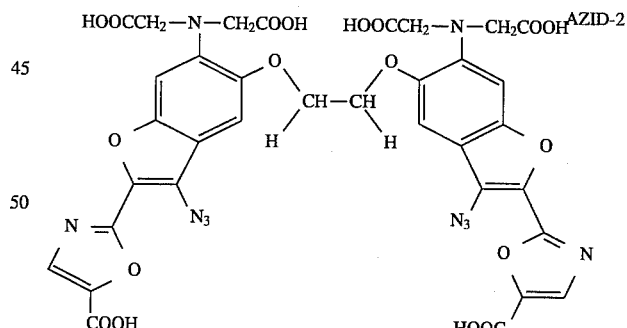

have a number of features which make them superior to the existing "caged calciums":

1. Upon photolysis, the chelator Azid-1 changes its $Ca^{2+}$ affinity from about 200 nM to 100 μM. This change of 500-fold is more than 10-fold greater than nitr-5 (which decreases affinity 40-fold, from 150 nM to 6 μM). With Azid-1 it is now feasible to produce changes of tens of micromolar concentration in free calcium rather than the more modest increases exhibited by the conventional nitr chelators.

2. Azid-1 also shows the high selectivity for $Ca^{2+}$ over $Mg^{2+}$ (greater than $10^4$-fold) similar to nitr chelators.

This property is in contrast to DM-nitrophen, which although capable of giving large $Ca^{2+}$ jumps like Azid-1, also binds $Mg^{2+}$ tightly. Under typical intracellular free concentrations of $Ca^{2+}$ and $Mg^{2+}$, DM-nitrophen has a poor effective affinity for $Ca^{2+}$ because $Mg^{2+}$ competes for the chelator. Only when $Mg^{2+}$ is removed does the high affinity for $Ca^{2+}$ reveal itself. DM-nitrophen has therefore been restricted to perfused cells or cell-free systems in which the relative concentrations of $Ca^{2+}$, $Mg^{2+}$ and DM-nitrophen can be controlled and in which removal of normal $Mg^{2+}$ can be tolerated. The $Ca^{2+}$ affinity of DM-nitrophen is also pH sensitive in the physiological range adding yet more uncertainty to its use in $[Ca^{2+}]_i$. The affinity of Azid-1 for $Ca^{2+}$ also shows much less pH sensitivity.

3. A major limitation of conventional nitr chelators is their relatively low sensitivity to ultraviolet light. The partial photolysis capable with a single pulse from a light source limits the size of the resulting increase in $Ca^{2+}$. Azid-1 is significantly more sensitive to UV light and produces much larger increases in $Ca^{2+}$ per flash. A measure of light-sensitivity of a molecule is the product of its quantum yield Q and the extinction coefficient $\epsilon$ at the irradiating wavelength. The higher the product $Q\epsilon$, the greater the light sensitivity. $Q_\epsilon$ values for nitr-5 and DM-nitrophen are 192 and 780 $M^{-1}cm^{-1}$, respectively. On the other hand, Azid-1 has a value of 33,000 $M^{-1}cm^{-1}$ (170- and 40-fold greater). This demonstrated increased photosensitivity permits the photolysis apparatus to be much simpler and cheaper, and also minimizes the likelihood that the illumination will perturb or damage the tissue. Furthermore, photolysis decreases the absorbance at the usual irradiation wavelengths of 350–365 nm, so that inner filtering actually decreases as photolysis proceeds.

4. In addition to the above properties, Azid-1 also releases $Ca^{2+}$ rapidly upon photolysis. Experiments show that $Ca^{2+}$ release is complete within 2 milliseconds (ms), the time-resolution of present equipment. This rate is already sufficient for many biological applications.

5. Concentrated solutions of the chelator suitable for microinjections are possible. Masking of the carboxylates present, as esters, e.g., acetoxymethyl (AM) esters permits loading of chelators into large numbers of cells or tissues in analogy to the related fluorescent $Ca^{2+}$ indicators.

The affinity of the chelator was photochemically manipulated through electronic rather than steric effects, by introducing a photosensitive group, e.g., an azide, onto a heteroaromatic ring in conjugation with the iminodiacetic acid moiety.

Synthesis of the Compounds of the Invention

The synthesis of the compounds of the present invention is described in general below.

Aldehyde—Compound 1 is prepared according to U.S. Pat. No. 4,603,209. Similar compounds are prepared using suitably substituted aldehydes.

Aldoxime—Compounds of the general structure for Compound 2 are produced by contacting the aldehyde with an alcohol and ether with hydroxylamine under ambient conditions. The reaction mixture is gently heated between about 20° and 90°, preferably 50°–70° C. and stirred overnight (about 20–24 hours). The product aldoxime is precipated by water, filtered, and purified by cystallization from alcohol.

Nitrile—Compound—3 type aldoximes are contacted in a halogenated hydrocarbon solvent with phosgene-iminum chloride. After reflux for 1 to 60 min, the solution is reduced to dryness using reduced pressure. The residue is taken up in an alcohol and cooled to 0° C. The precipitate is separated by filtration and washed with cold alcohol to produce the nitrile.

Cyanophenol—The substituted nitrile is hydrogenated to produce the cyanophenol. This can be accomplished by a number of hydrogenation methods known in the art. A preferred method is to catalytically hydrogenate the nitrile at ambient conditions using, for example, palladium on carbon in the presence of mixed solvents, such as organic acetates and organic acids (e.g. ethyl acetate: acetic acid). The reaction product is filtered and the filtrate is reduced to dryness. Recrystallization from alcohol produces the cyanophenol.

Heteraromatic (Oxazole) Amine—The cyanophenol is contacted with a suitable 2-halomethyl (heteroaromatic group) carboxylate in dipolar aprotic solvent (DMF) with anhydrous potassium carbonate under anhydrous conditions at about 100° to 150° C., preferably about 130° C., for about 0.5–3 hours, preferably about 1 hour. The cooled reaction mixture is diluted with water and acidified using acetic acid, and extracted with ethyl acetate. The extract is dried, evaporated to dryness using reduced pressure to produce crude oxazole amine. Purification by chromatography and recrystallization produced purified heteroaromatic amine.

Azide—The Azide (e.g., Compound 6) is produced by contacting the oxazole amine (Compound 5) with cold glacial acetic acid which is slowly added to an aqueous solution of nitroso sulfuric acid and sulfuric acid. After 10 to 60 minutes, the reaction mixture is added slowly and carefully to an ice-cold saturated aqueous sodium azide with vigorous stirring (in a fume hood). After neutralization (e.g. using sodium bicarbonate), the reaction mixture is diluted with water and extracted (e.g. ethyl acetate). After drying the extract was reduced to dryness yielding crude azide which was further purified using column chromatography.

Azid-2—The preparation of compounds having two active azide groups is described. Two equivalents of starting material (as described in Grynkiewicz, et. al. U.S. Pat. No. 4,603,209 for the 4-benzyloxy 2-nitrophenol, intermediate XX1) is contacted with one equivalent of 1, 2-dibromoethane in the anhydrous potassium carbonate and dimethylformamide produces the 1,2-bis(4-benzyloxy-2-nitrophenoxy) ethane. This material is then subjected to the experimental conditions described above, or in the Examples to produce Azid-1, to produce the corresponding compound having two active azide groups.

The following Examples are presented for the purposes of illustration and description only. They are not to be construed as being limiting in any way.

COMPOUND SYNTHESES

Chemicals and solvents (high performance liquid chromatography-HPLC-grade) were used directly as obtained unless otherwise noted. Chloroform and dimethylformamide were dried over 4A molecular sieves.

Proton magnetic resonance spectra ($^1$H NMR) were recorded on a Gemini 200 -MHz spectrometer in $CDCl_3$ unless otherwise noted, and the chemical shifts are given in δ values relative to tetramethylsilane. Ultraviolet (UV) absorbance spectra were recorded on a Perkin-Elmer Lambda Array 3840 spectrophotometer at 20±2° C.

Thin layer chromatography (TLC) was carried out on precoated silica gel 60F-254 (E. Merck) or reverse-phase (RP-18, F-254, E. merck, or $MKC_{18}F$, Whatman) plates. For column chromatography, silica gel 60 (230–400 mesh, E. Merck) was used. All manipulations of compounds sensitive to near ultraviolet light were performed under an orange safety lamp.

COMPOUND 2

Salicylaldoxime

Compound 1 (The aldehyde prepared as described in U.S. Pat. No. 4,603,209) (1.0 g, 1.36 mmol) dissolved in dioxane (6 ml) and methanol (6 ml) was treated with a solution of hydroxylamine hydrochloride (278 mg, 4 mmol) and sodium acetate (230 mg, 2.8 mmol) dissolved in water (2.8 ml) at room temperature. After gentle warming to 60° C. to dissolve any solids, the reaction mixture was kept overnight at ambient (room) temperature. The product was precipitated by the addition of water (10 ml) and collected by filtration. Recrystallization from 95% ethanol yielded compound 2 as white crystals. Yield, 0.98 g (95%).

$^1$NMR δ 1.16 (t, 12H, $OCH_2CH_3$), 2.25 (s, 3H, $ArCH_3$,), 4.1 (2q, 8H, $OCH_2CH_3$), 4.20 (2S, 8H, $NCH_2$), 4.24 (s, 4H $OCH_2CH_2O$), 5.00 (s, 2H, benzyl $CH_2$) 6.39, 6.7 (m, 6H, aromatic), 7.35 (s, 1H, oxime OH), 7.38 (m, 5H, phenyl), 8.45 (s, 1H, CH=).

COMPOUND 3

Nitrile

A solution of compound 2 (0.98 g, 1.31 mmol) in $CHCl_3$ was added in one portion to a suspension of phosgene iminium chloride (0.36 g, 2.2. mmol) in chloroform (5 ml). After 10 minutes reflux, during which HCl fumes are evolved, the resulting solution was evaporated to dryness, and the residue boiled with methanol (50 ml). After cooling in ice, compound 3 was collected by filtration and washed with several portions of cold methanol. Yield 0.83 g (87%).

$^1$NMR δ 1.16 (2t, 12H, $OCH_2CH_3$), 2.26 (s, 3H, $ArCH_3$), 4.06 (2q, 8H, $OCH_2CH_3$), 4.11 (2S, 8H, $NCH_2$), 4.20 (s, 4H $OCH_2CH_2O$), 5.12 (s, 2H, benzyl $CH_2$) 6.31, 6.7, 7.00 (s, m, s, 6H, aromatic), 7.39 (m, 5H, phenyl).

COMPOUND 4

Cyanophenol

Compound 3 (300 mg, 0.41 mmol) was catalytically hydrogenated at room temperature and pressure with 300 mg of 5% Pd/C in ethyl acetate:acetic acid (1:2 v/v). Uptake was complete in 30 mins. The reaction mixture was filtered and evaporated to dryness to yield the product, compound 4. Recrystallization from ethanol gave a pale yellow solid. Yield 226 mg (86%).

$^1$NMR δ 1.2 (m, 12H, $OCH_2CH_3$), 2.26 (s, 3H, $ArCH_3$), 4.1 (2q, 8H, $OCH_2CH_3$), 4.17, (2S, 8H, $NCH_2$), 4.20 (m, 12H, $OCH_2CH_2O,NCH_2$), 6.26, 6.7 (m, 6H, aromatic).

COMPOUND 5

Oxazole Amine (a) Compound 4 (100 mg, 0.155 mmol), ethyl 2-chloromethyloxazole-5-carboxylate (30 mg, 0.16 mmol; prepared as described in U.S. Pat. No. 4,603,209) and anhydrous potassium carbonate (30 mg, 0.22 mmol) were heated in dry dimethylformamide (0.25 ml) at 130° C. for 1 hour under an argon atmosphere. The cooled reaction mixture was diluted with water (5 ml), acidified with acetic acid and extracted (3×5 ml) with ethyl acetate. After drying over sodium sulfate, the extract was evaporated to dryness to yield crude compound 5, that was further purified by silica gel chromatography eluting with ethyl acetate/hexane. The resulting yellow solid was triturated with isopropyl ether and filtered. Yield 71 mg (61%).

$^1$NMR δ 1.2 (2t, 12H, $OCH_2CH_3$), 1.40 (t, 3H, oxazole $OCH_2CH_3$), 2.27 (s, 3H, $ArCH_3$), 4.1 (2q, 8H, $OCH_2CH_3$), 4.2 (br m, 14H, $NCH_2OCH_2CH_2O$, $NH_2$), 4.41 (q, 2H, oxazole $OCH_2CH_3$), 6.70 (m, 3H, benzene), 6.85, 7.23 (2s, 2H, benzofuran), 7.86 (s, 1H, oxazole).

This structure itself when saponified has surprisingly interesting and useful properties as a fluorescent indicator for calcium ion.

(b) Similarly, when the ethyl 2-chloromethyloxazole-5-carboxylate is replaced by a stoichiometrically equivalent amount of the structures shown below:

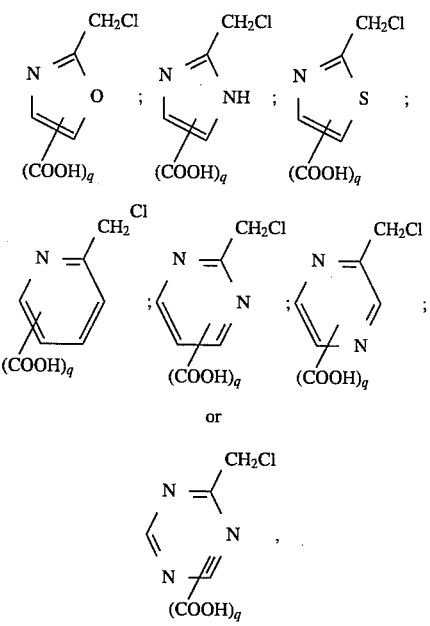

and q is 0, 1 or 2, the corresponding heterocyclic amine compounds are expected to be obtained and are further used by adaption of the following reactions to produce the mono- and di-azide compounds of the present invention.

COMPOUND 6

Azid-1 Pentaethyl Ester

Compound 5 (20 mg, 26.4 μmol) was dissolved in cold glacial acetic acid (300 μl) and added dropwise with stirring to a solution of nitroso sulfuric acid (20 mg, 157 μmol; Lancaster Synthesis) in concentrated sulfuric acid (200 μl) at 0° C. After 20 mins., the reaction mixture was added dropwise to a ice-cold saturated aqueous solution of sodium azide (20 ml) with vigorous stirring (Caution: hydrazoic acid is generated; carry out in well-ventilated fumehood). After neutralization with solid sodium bicarbonate, the mixture was diluted with water and extracted (3×20 ml) with ethyl acetate. Drying over sodium sulfate and evaporation to dryness yielded crude compound 6 which was further purified by silica gel column chromatography eluting with ethyl acetate/hexane and trituration with ethanol. Yield of pale yellow solid, 13.5 mg (66%).

$^1$NMR δ 1.16 (m, 12H, OCH$_2$CH$_3$), 1.38 (t, 3H, oxazole OCH$_2$CH$_3$), 2.27 (s, 3H, ArCH$_3$), 4.05 (q, 8H, OCH$_2$CH$_3$), 4.10, 4.22 (2s, 8H, NCH$_2$), 4.32 (s br 4H, OCH$_2$CH$_2$O), 4.43 (q, 2H, oxazole OCH$_2$CH$_3$) 6.70 (m, 3H, benzene), 6.95, 7.13 (2s, 2H, benzofuran), 7.91 (s, 1H, oxazole).

COMPOUND 7

Azid-1 Pentapotassium Salt

Azid-1 pentaethyl ester, Compound 7 was saponified to the penta-anion by dissolution in dioxane-methanol (1:1 v/v), addition of an excess of aqueous 1M potassium hydroxide and keeping at room temperature overnight.

COMPOUND 8

Chelator Having Two Azide Groups (Azid-2)

The reaction of 2 equivalents of 4-benzyloxy-2-nitrophenol (intermediate XX1, Grynkiewicz et al, 1986; U.S. Pat. No. 4,603,209) with 1 equivalent of 1,2-dibromoethane in the presence of potassium carbonate and dimethylformamide at 140° C. for 5 hours produces 1,2-bis(4-benzyloxy-2-nitrophenoxy)ethane. Analogous treatment of this compound with the sequence of reactions used to produce azid-1 in FIG. 5 produces the difunctionalized azide, Azid-2.

EXAMPLE 1

Calcium and Magnesium Affinities

Ca$^{2+}$—binding constants for chelators before and after photolysis were determined by monitoring UV spectra during titration of EGTA buffers to varying free Ca$^{2+}$ levels and by adding aliquots of standard solutions of CaCl$_2$ to nominally Ca-free solutions respectively.

Either the ratio of, for example, [Ca,EGTA] to free [EGTA] was adjusted at a constant pH, or the pH was varied while [CaEGTA]=[EGTA]. These two approaches gave equivalent answers for pH greater than 7 whenever directly tested, because of the pH insensitivity of BAPTA-like ligands. The apparent dissociation constants of Ca,EGTA were calculated as described by R. Y. Tsien (1980). For titration of the weak binding constants of photolysed chelators, the Ca$^{2+}$ negligible (a few micromolar).

Free [Mg$^{2+}$] was likewise controlled by Mg/EGTA buffers, assuming an apparent dissociation constant for Mg,EGTA complex (including its monoprotonated form) of 6 mM at pH 7.60 in 0.1M ionic strength; see R. Y. Tsien, et al. (1986).

EXAMPLE 2

Quantum Efficiencies of Photolysis

The photolysis quantum efficiencies of Azid chelators were determined by alternately irradiating and measuring the absorbance spectrum of a buffered solution of the substrate with a known intensity of longwave UV light, in apparatus described by S. R. Adams, et al. (1988).

EXAMPLE 3

Flash Photolysis

Flash photolysis of Azid chelators and the concomitant monitoring of free Ca$^{2+}$ concentration with fluo-3, a fluorescent Ca$^{2+}$-indicator, were performed using methodology and instrumentation described in A. Minta, et al. (1989) and J. P. Y. Kao, et al. (1989). Briefly, output from a Xe arc lamp was passed through a monochromator to yield the 490 nm light used to probe the fluo-3 indicator. The fluo-3 intensity from droplets (approximately 50–100 μm diameter) of buffered aqueous solutions of part Ca$^{2+}$-loaded Azid-1 and fluo-3 under mineral oil on a inverted fluorescence microscope stage, was recorded by a photomultiplier and processed by a SpexDM3100 spectrofluorimeter. Photolyses were performed by triggering a xenon flash lamp (Strobex Model 238) through a UV bandpass filter (Rolyn Optics, UG-1) placed in the excitation path of the Zeiss fluorescence microscope. A custom dichroic mirror (DR505LP UV-enhanced, Omega Optical, Inc.) was placed in the microscope epifluorescence filter cube to reflect both UV and 490 mm light while retaining transmission at wavelengths >510 nm, where fluo-3 emits strongly.

EXAMPLE 4

In Vivo Biological Tests

For a preliminary biological test, Fisher rat embryo fibroblast of the REF52 cell line were cultured as described by J.P.Y. Kao, et al. (1988).

For testing Azid-1, REF52 cells in Hanks balanced salt solution, buffered to pH 7.4 with HERPES, were microinjected with a buffered solution of Azid-1 (50–100 mM) and fluo-3 (10 mM) potassium salts, on a microscope stage at 25° C. Flash photolysis of the Azid-1 and concomitant monitoring of the intracellular free Ca$^{2+}$ concentration with fluo-3 were performed using methodology described in A. Minta, et al. (1989), J.P.Y. Kao, et al. (1989) and U.S. Pat. No. 5,141,627. Photolysis is performed by briefly moving a chopper mirror to send output from xenon arc lamp which had been passed through a monochromator to yield the 365 nm light. The fluorescent images of cells were recorded by a SIT TV camera and processed by a Micro-PDP-1183 computer.

While only a few embodiments of the present invention have been shown and described herein, it will become apparent to those skilled in the art that various modifications and changes can be made in these azide-containing chelators whose affinity is for calcium ion is decreased by illumination without departing from the spirit and scope of the present invention. All such modifications and changes coming within the scope of the appended claims are intended to be carried thereby.

We claim:

1. An azide compound of the formula:

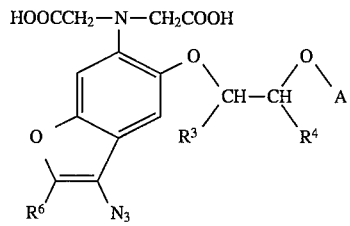

and the pharmaceutically acceptable non-toxic salts and esters thereof, wherein:

A is

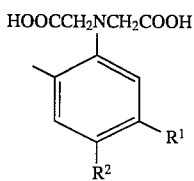

$R^1$ and $R^2$ are each independently selected from the group consisting of —H, and $C_1$ to $C_4$ alkyl, —F, —Cl, —Br, —$C_1$ to $C_4$ alkoxy, —$NO_2$, —$COO^-$, and —$NH(C=O)R^5$, where $R^5$ is —H, or $C_1$ to $C_{18}$ alkyl;

$R^3$ and $R^4$ are each independently selected from the group consisting of —H, and $C_1$ to $C_4$ alkyl, and $R^6$ is an isoxazole group, said isoxazole group having 0, 1 or 2 ring substituents.

2. The compound of claim 1 wherein A is:

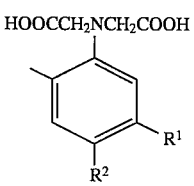

and $R^1$ is hydrogen.

3. The azide compound of claim 2 wherein $R^2$ is $C_1$ to $C_4$ alkyl.

4. The azide compound of claim 1 wherein $R^1$, $R^3$ and $R^4$ are each hydrogen.

5. The azide compound of claim 4 wherein $R^2$ is alkyl $C_1$ to $C_4$.

6. The azide compound of claim 5 wherein $R^2$ is methyl, and $R^1$ is hydrogen.

7. The compound of claim 6 wherein $R^6$ is

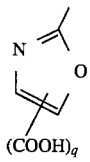

and q is 0, 1 or 2.

8. The compound of claim 7 wherein $R^3$ and $R^4$ are each hydrogen, q is 1.

9. The azide compound of claim 8 wherein $R^6$ is:

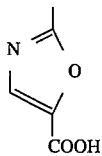

10. The azide compound of claim 2 as the physiologically acceptable non-toxic ester.

11. The azide compound of claim 1 as the physiologically acceptable non-toxic methyl, ethyl, propyl, butyl, acetoxymethyl, 1-acetoxyethyl, formyloxymethyl, pivaloyloxymethyl, dimethylaminoethyl, or diethylaminoethyl ester.

12. The azide compound of claim 2 as the physiologically acceptable non-toxic salt.

13. The azide compound of claim 2 as the physiologically acceptable non-toxic free acid.

14. The fluorescent indicator of the structure:

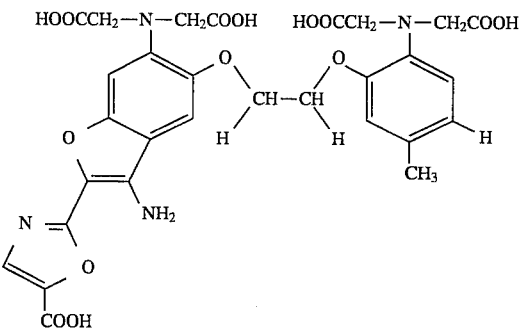

and the esters, free acids, or salts thereof.

15. The azide compound of claim 8 wherein $R^6$ is

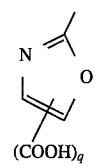

and q is 2.

16. The azide compound of claim 2 wherein $R^3$ and $R^4$ are each hydrogen, $R^2$ is methyl; and $R^6$ is a substituted oxazole.

17. The azide compound of claim 2 wherein $R^3$ and $R^4$ are each hydrogen;

$R^6$ is

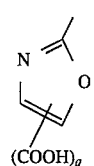

wherein q is 2.

18. A fluorescent indicator of the formula:

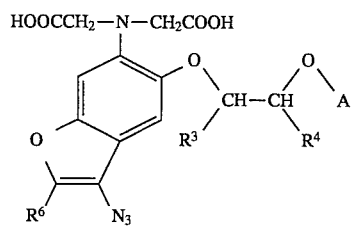

and the pharmaceutically acceptable non-toxic salts and esters thereof, wherein:

A is

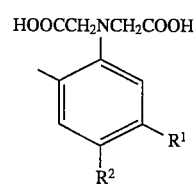

$R^1$ and $R^2$ are each independently selected from the group consisting of —H, $C_1$ to $C_4$ alkyl, —F, Cl, —Br, $C_1$ to $C_4$ alkoxy, and —$NO_2$;

$R^3$ and $R^4$ are each independently —H, $C_1$ to $C_4$ alkyl, —$CH_2OH$ or —COOH; and $R^6$ is an isoxazole group, said isoxazole group having 1 or 2 ring substituents.

19. The fluorescent indicator of claim 18 wherein $R^1$, $R^3$ and $R^4$ are each hydrogen, and $R^2$ is methyl.

20. The fluorescent indicator of claim 18 wherein $R^6$ is an oxazole which is substituted with at least one —COOH group.

21. The fluorescent indicator of claim 20 wherein $R^6$ is an oxazole which is substituted with two —COOH groups.

* * * * *